United States Patent

Huber et al.

[11] Patent Number: 5,941,847
[45] Date of Patent: Aug. 24, 1999

[54] BREAST SHIELD WITH VACUUM ISOLATION ELEMENT

[75] Inventors: Anthony Huber, Zug; Beat J. Moser, Baar, both of Switzerland

[73] Assignee: Medela Holding AG, Switzerland

[21] Appl. No.: 09/019,990

[22] Filed: Feb. 6, 1998

[51] Int. Cl.⁶ .................................................. A61M 1/06
[52] U.S. Cl. ............................................................ 604/74
[58] Field of Search .................... 604/73–76, 118, 604/119, 313–316; 119/14.23, 14.32, 14.46, 14.49

[56] References Cited

U.S. PATENT DOCUMENTS

| | | |
|---|---|---|
| 316,584 | 4/1885 | Turner . |
| 532,236 | 1/1895 | Hardesty . |
| 684,078 | 10/1901 | Martin . |
| 956,325 | 4/1910 | Fey . |
| 975,047 | 11/1910 | Klein et al. . |
| 1,113,942 | 10/1914 | Anderson . |
| 1,156,202 | 10/1915 | Barrett . |
| 1,184,631 | 5/1916 | De Leon . |
| 1,460,927 | 7/1923 | Thompson et al. . |
| 1,644,257 | 10/1927 | Lasker . |
| 1,670,610 | 11/1926 | Colby . |
| 2,000,710 | 5/1935 | Miller . |
| 2,060,063 | 11/1936 | Frimand . |
| 2,222,811 | 11/1940 | Dinesen . |
| 2,419,795 | 4/1947 | Saunders . |
| 2,522,108 | 9/1950 | Flagg . |
| 2,542,505 | 2/1951 | Gascoigne . |
| 2,545,857 | 3/1951 | Perkins et al. . |

(List continued on next page.)

FOREIGN PATENT DOCUMENTS

| | | |
|---|---|---|
| 831799 | 7/1975 | Belgium . |
| 0 733 376 A2 | 3/1996 | European Pat. Off. . |
| 599054 | 1/1926 | France . |
| 540934 | 12/1931 | Germany . |
| 24 51 953 | 5/1976 | Germany . |
| 28 07 646 | 8/1978 | Germany . |
| 251810 | 11/1947 | Switzerland . |
| 2 995 | of 1911 | United Kingdom . |
| 17778 | of 1915 | United Kingdom . |
| 168234 | 9/1921 | United Kingdom . |
| 271857 | 10/1927 | United Kingdom . |
| 660283 | 11/1951 | United Kingdom . |
| 762701 | 12/1956 | United Kingdom . |

OTHER PUBLICATIONS

"Mother's Touch; one–hand breast pump", Circle Caring, Ameda/Egnell Corp.

"Breastfeeding; a Guide for the Medical Profession", Ruth A. Lawrence, M.D., pp. 467–469.

"Medela Manual Breastpump/Feeding System" Medela.

*Primary Examiner*—Wynn Wood Coggins
*Assistant Examiner*—Sharon Finkel
*Attorney, Agent, or Firm*—Baniak Nicholas Pine & Gannon

[57] ABSTRACT

A breast shield is provided that includes a hood body with an outer rim within which a breast is received and a shield extension portion extending downstream from the outer rim. A milk drain is connected to the shield extension portion. A vacuum isolation element including a collapsible membrane is connected to the shield extension portion of the hood body. The collapsible membrane portion includes an interior cavity communicating with the vacuum source. The interior cavity is effective to create a negative pressure within the shield extension portion when collapsed by vacuum to isolate the vacuum source from expressed milk, with milk being channelled through the insert to a collector, such as a milk bottle.

20 Claims, 3 Drawing Sheets

U.S. PATENT DOCUMENTS

| | | |
|---|---|---|
| 3,032,037 | 5/1962 | Huber . |
| 3,233,607 | 2/1966 | Bolie . |
| 3,382,867 | 5/1968 | Reaves . |
| 3,587,567 | 6/1971 | Schiff . |
| 3,738,363 | 6/1973 | Lunas et al. . |
| 3,782,385 | 1/1974 | Loyd . |
| 3,822,703 | 7/1974 | Davisson . |
| 3,830,238 | 8/1974 | Kurtz et al. . |
| 3,911,920 | 10/1975 | Susinn . |
| 3,977,405 | 8/1976 | Yanase . |
| 4,249,481 | 2/1981 | Adams . |
| 4,263,912 | 4/1981 | Adams . |
| 4,311,141 | 1/1982 | Diamond . |
| 4,323,067 | 4/1982 | Adams . |
| 4,573,969 | 3/1986 | Schlensog et al. . |
| 4,583,970 | 4/1986 | Kirchner . |
| 4,634,430 | 1/1987 | Polaschegg . |
| 4,673,388 | 6/1987 | Schlensog et al. . |
| 4,680,028 | 7/1987 | Stuart . |
| 4,759,747 | 7/1988 | Aida et al. . |
| 4,775,366 | 10/1988 | Rosenblatt . |
| 4,794,915 | 1/1989 | Larsson . |
| 4,799,922 | 1/1989 | Beer et al. . |
| 4,799,924 | 1/1989 | Rosenblatt . |
| 4,799,925 | 1/1989 | Rosenblatt . |
| 4,857,051 | 8/1989 | Larsson . |
| 4,883,464 | 11/1989 | Morifuki . |
| 4,929,229 | 5/1990 | Larsson . |
| 4,961,726 | 10/1990 | Richter . |
| 5,007,899 | 4/1991 | Larsson . |
| 5,009,638 | 4/1991 | Riedweg et al. . |
| 5,049,126 | 9/1991 | Larsson . |
| 5,100,406 | 3/1992 | Panchula . |
| 5,358,476 | 10/1994 | Wilson . |

BREAST SHIELD WITH VACUUM ISOLATION ELEMENT

FIELD OF THE INVENTION

The present invention relates generally to a breastmilk pump and, more particularly, relates to a breast shield having a vacuum isolation element.

BACKGROUND OF THE INVENTION

Breast pumps are well known, and generally comprise a hood or shield that fits over the breast, a vacuum pump connected to the hood for generating an intermittent vacuum (or negative pressure) within the hood, and a receptacle for expressed milk. The intermittent suction action of the vacuum pump serves to pull on the breast and nipple and thereby extract milk. The extracted milk typically flows from the hood into a collection container for storage and later use. A breast pump of the foregoing type is shown in Larsson U.S. Pat. No. 4,857,051, the disclosure of which is incorporated herein by reference for further details of a breast pump assembly in general.

Inserts for use within the hood of a breast pump are known, but they have typically been used for sizing the breast shield. A flexible breast engaging device has also been used for nipple stimulation, as disclosed in Larsson U.S. Pat. No. 5,049,126. The '126 patent discloses a frame made from a rigid material having a funnel shape. A flexible membrane fits over the nipple receptor frame. When suction is applied to the flexible membrane, it collapses and gently squeezes the nipple for inducing uterine activity.

While various prior art breast pump constructions have been quite effective, there are certain drawbacks associated with some of these constructions. For example, there has been a problem with bacteriological contamination is some previous breast pumps when a motor driven pump is used. Overflow protection is necessary to prevent milk from entering the pump air line. Even so, it has been found that moisture and the like from the user may still enter the pump air line.

Another design consideration for breast pumps is associated with the maintenance of the breast pump in a sanitary condition. In particular, depending upon the configuration of the interior walls of the hood body, it can be difficult for some users to properly clean the device. More specifically, the internal wall construction of the hood body of some previous constructions can have crevices and small passageways that are not easily cleaned.

Accordingly, it is desirable in a breast pump assembly to reduce contamination of the motor air line associated with certain motor driven pumps, and to provide a breast pump that is easily cleaned by a user.

SUMMARY OF THE INVENTION

Briefly stated, the present invention is directed to an improved breast shield assembly for use with a collector for expressed milk and a vacuum source. A breast shield assembly is provided that includes a hood body (or shield) with an outer rim within which a breast is received and a hood extension portion extending downstream from the outer rim. A milk drain communicates with the hood extension portion. In a preferred embodiment, a vacuum isolation element including a collapsible membrane is located in the shield extension portion of the hood body. The collapsible membrane portion includes an interior cavity adapted to be connected to the vacuum source. A portion forms a conduit or passageway from the extension portion to the milk drain. The interior cavity is effective to create a negative pressure within the shield extension portion when in a collapsed state, and isolate the vacuum from expressed milk, with milk being channelled through the isolation element to a collector, such as a milk bottle.

According to another aspect of the invention, the vacuum isolation element is a monolithic (single piece) insert which is removably received in the hood of the breast shield. A further aspect of the invention is that the vacuum isolation includes a valve located within the milk drain.

A noteworthy advantage of the present invention is that the use of the vacuum isolation element can substantially prevent bacteriological contamination of the pump assembly. The vacuum isolation element serves as a liner to the breast shield, to prevent air or milk from within the hood from contaminating the breast shield or damaging the pump.

Another advantage of the present invention is that the vacuum isolation element can be removable and even made disposable. Because the vacuum isolation element is the only portion of the assembly that is in direct contact with the expressed milk, the breast shield assembly can be more easily and reliably cleaned.

The present invention will be further understood with reference to the detailed description below read in conjunction with the accompanying drawings, in which:

DETAILED DESCRIPTION OF AN EMBODIMENT

Figure 1:
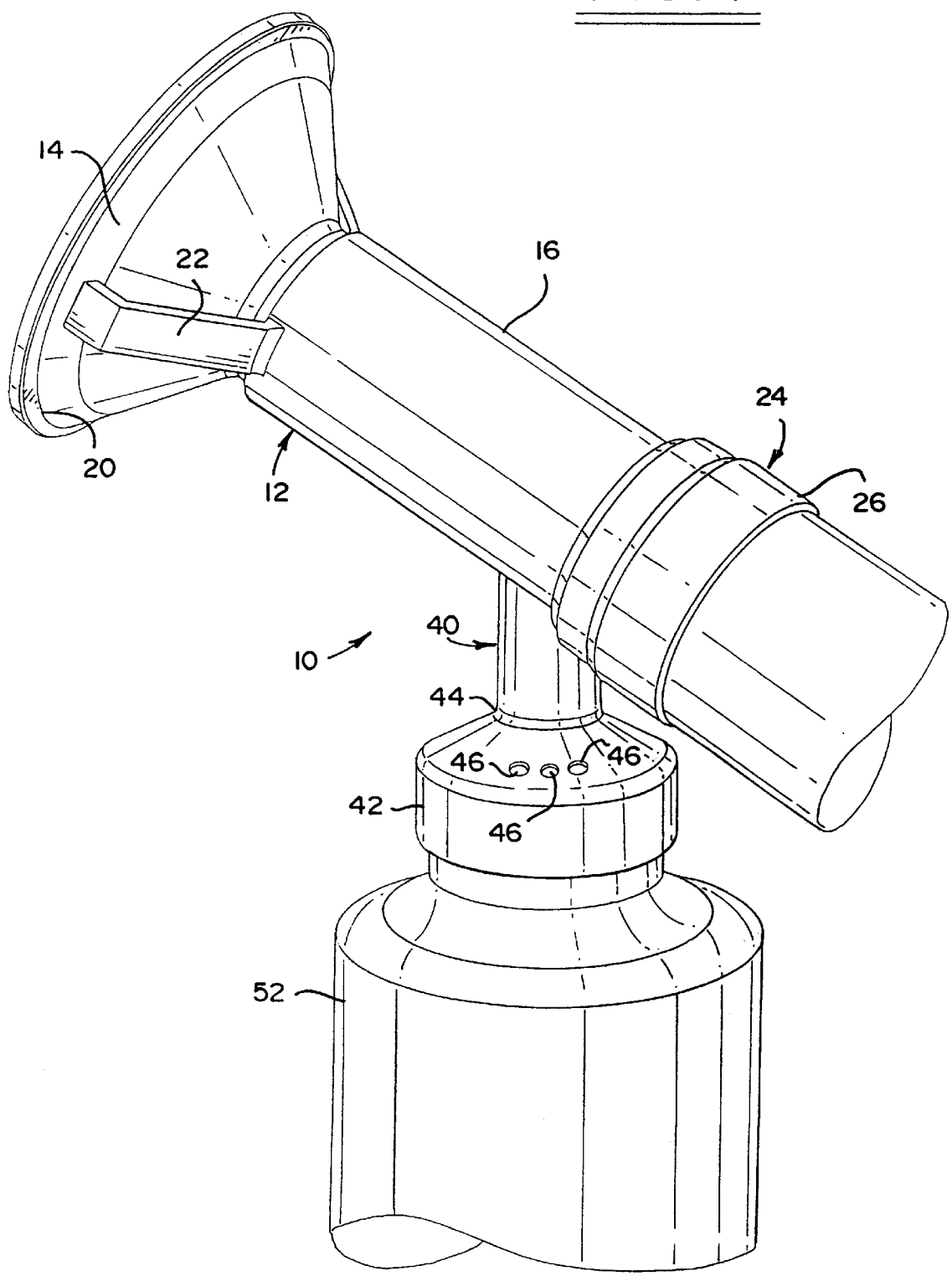
FIG. 1 is an assembled view of a preferred embodiment of a breast pump including a breast shield and vacuum isolation element constructed in accordance with the present invention.

FIG. 1 illustrates a preferred embodiment of a breast pump 10 constructed in accordance with the present invention. A hood body or shield 12 having an outer rim 14 and an extension portion 16 is illustrated. The outer rim 14 forms a circular opening 18 on the first end 20 of the hood body 12. Two support braces 22 connect the outer rim 14 to the extension portion 16, and define a shell for the hood body 12. As those of ordinary skill in the art will recognize, a wide variety of sizes may be used to construct a hood body in accordance with the present invention.

Figure 3:
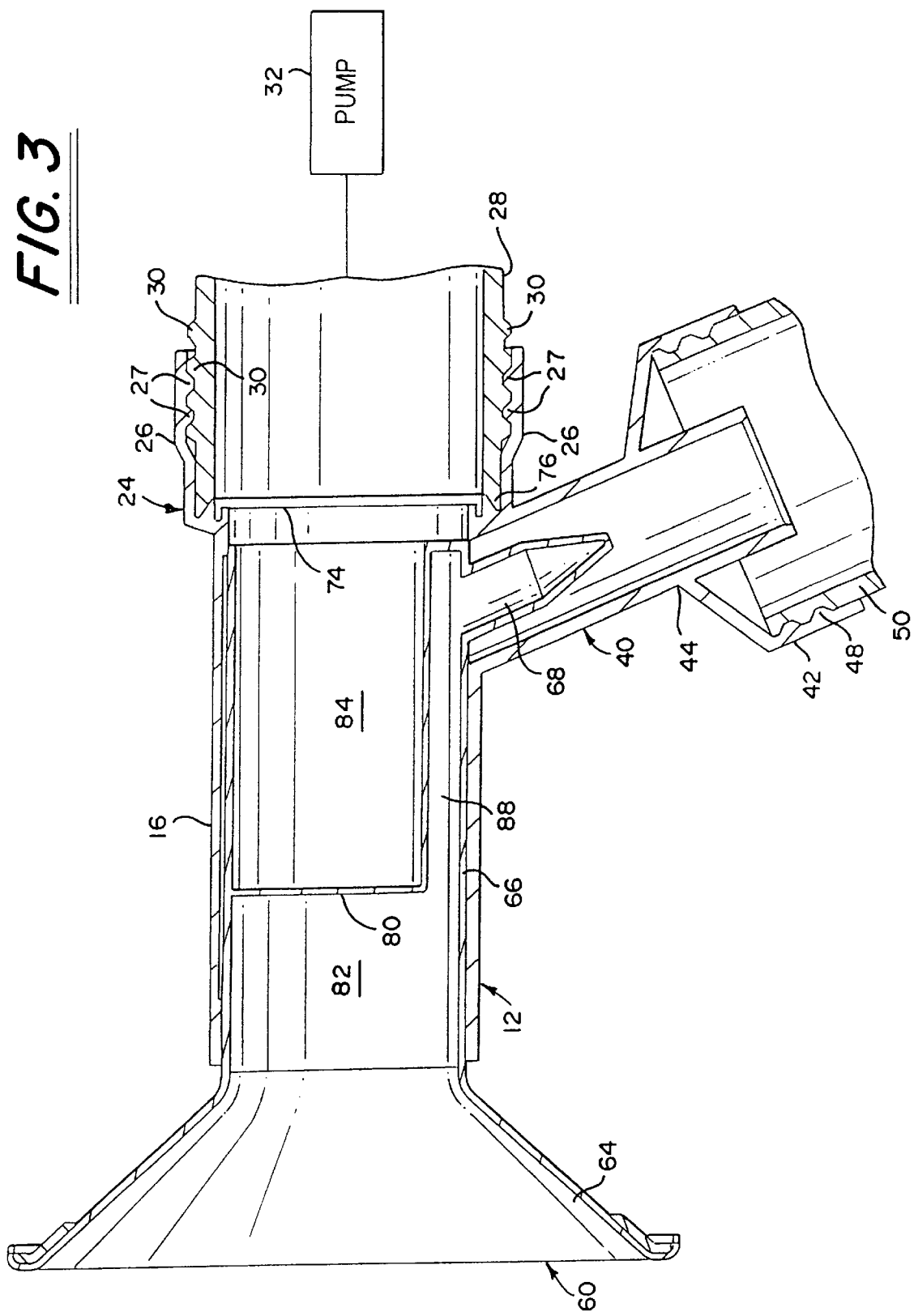
FIG. 3 is an enlarged sectional view of the breast shield and vacuum isolation element as shown in FIG. 1.

The extension portion 16 takes the forms of tube or cylinder in the preferred embodiment shown in the drawings. The diameter of the extension portion 16 is substantially narrower than the diameter of the outer rim 14. The second end 24 of the hood body 12 includes a collar 26 having a threaded interior surface 27 for connection to a vacuum source. As illustrated in FIG. 3, the pump collar 28 includes a threaded exterior surface 30 that mates with the threaded interior surface 27 in order to secure the pump collar 28 to the hood body 12. The pump collar 28 is connected to a pump 32 operable to create a vacuum. It is important to recognize that the vacuum source could include a motor driven pump or a manual pump. In addition, it should also be recognized that attachment mechanisms other than threaded engagement could be used to connect the vacuum source to the hood body 12, such as a snap-fit type attachment mechanism. Again, reference may be made to U.S. Pat. No. 4,857,051 for such details as to the use and engagement of various vacuum sources.

A milk drain or transfer 40 also communicates with the extension portion 16 of the hood body 12. In the preferred embodiment, the milk drain 40 takes the form of a tube or cylinder on a lower portion of the hood body 12. A catch chamber attachment collar 42 is formed at the base 44 of the milk drain 40. The attachment collar 42 has air pressure relief openings 46 (FIG. 1). The attachment collar 42 has a threaded interior surface 48 that mates with correspondingly threaded surface 50 on a catch chamber or milk bottle 52, which collects the expressed milk.

Figure 2:
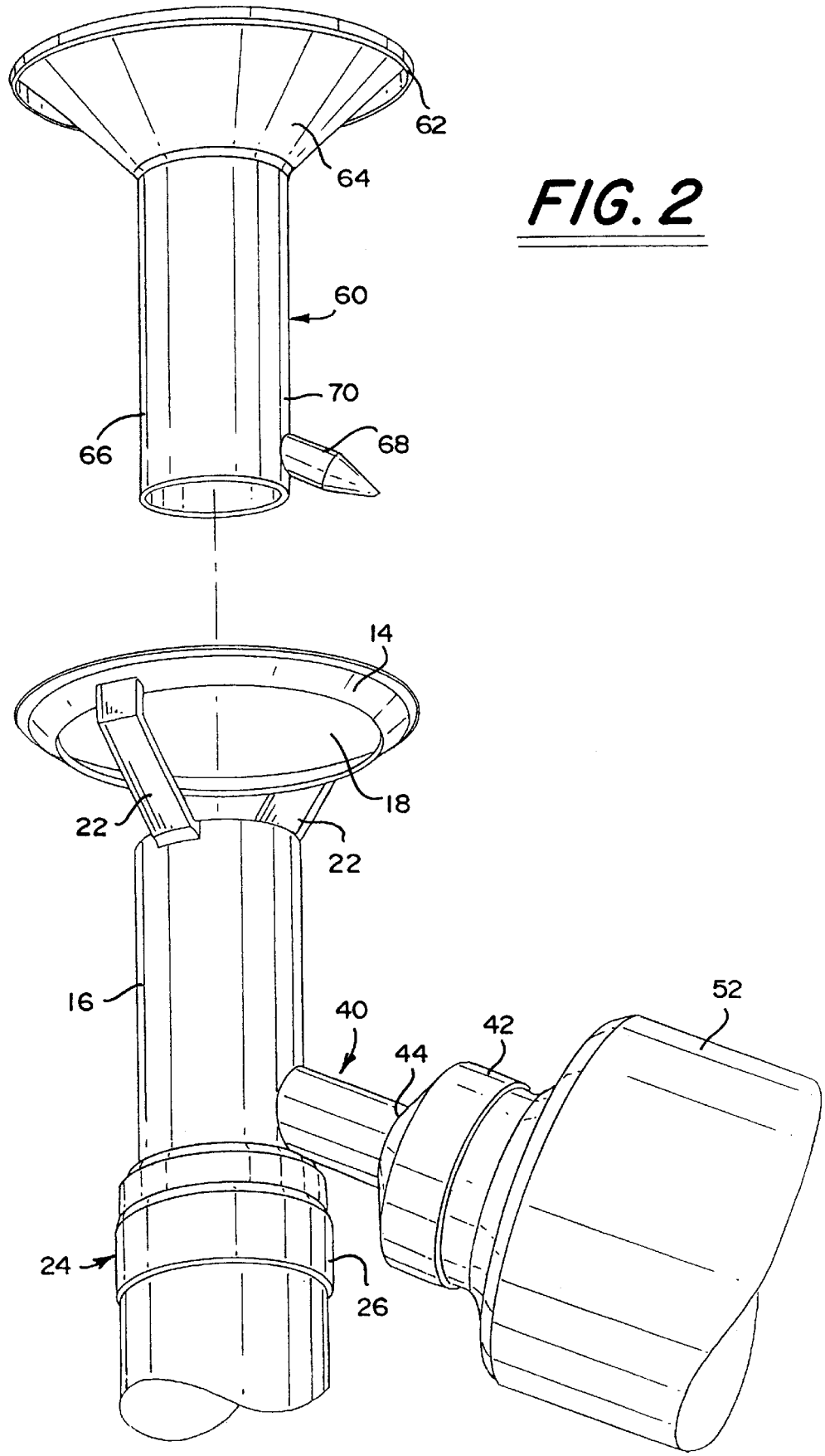
FIG. 2 is an exploded view of a breast shield and vacuum isolation element as shown in FIG. 1.

The insert 60 is best seen in FIG. 2. The insert 60 includes a first lip 62 having an internal channel that overlays and is secured around the outer rim 14 when assembled. A hemispherical or cone-shaped part 64 extends downward from the lip 62 to the beginning of the extension portion 16 of the hood body 12, and receives the breast of a user. A tubular extension portion 66 extends from the hemispherical shaped part 64. The hemispherical part and the tubular portion 16 form a funnel. When assembled, the tubular portion 66 is received within the extension portion 16. A duck-bill type valve 68 extends from a lower portion 70 of the insert 60. A second lip 74 extends from the downstream end of the insert 60. The second lip 74 extends over a rear rim 76 of the hood body 12 and seals the assembly when the pump collar 28 is connected thereto. The entire insert 60 is made of a thin flexible latex.

As best seen in FIG. 3, a collapsible membrane 80 is formed within the interior 82 of the tubular portion 66. In this embodiment, the collapsible membrane 80 is also generally tubular, or cylindrical, in shape. An interior cavity 84 is defined by the collapsible membrane 80. This cavity 84 communicates with the vacuum source through the collar 26 and the pump collar 28 connection. The vacuum source, therefore, is sealed from contact with the interior 82 of the insert 60. A milk passageway 88 extends adjacent the collapsible membrane 80.

It should be recognized that the collapsible membrane 80 can be formed in other shapes or configurations than the one illustrated in the FIGURES. For example, while in one preferred embodiment the collapsible membrane 80 occupies greater than 50% of the volume of the interior 82 of the tubular portion 66 of the insert 60, other sizes may be implemented. The volume of the collapsible membrane is sized as needed to transmit sufficient negative pressure from the vacuum source to the breast within the funnel to adequately pull upon the breast for milk expression. Also, as noted, in the preferred embodiment, the insert 60 is formed as a one-piece or monolithic element from latex, or could be formed from materials such as silicone. However, as those of ordinary skill in the art will recognize, use of other materials or configurations is possible.

In use, the insert 60 is placed within the hood body 12 as illustrated in FIG. 1. A user places her breast within portion 64 of the insert 60. A negative pressure is created within the interior 82 of the insert 60 through operation of the vacuum source in order to draw upon the user's breast. More specifically, the vacuum is transmitted into cavity 84 which causes the collapsible membrane 80 to collapse, thereby creating a negative pressure in the interior 82 of the insert 60. The nipple and adjacent breast are thereby drawn into the interior 82. Milk is expressed into milk passageway 88. When the negative pressure is released from interior 82 by stopping the vacuum and applying a positive pressure, the milk is released through the valve 68 into the milk bottle 52.

The embodiment described is illustrative and not restrictive. The scope of the invention is indicated by the claims rather than by the foregoing description. The invention may be embodied in other specific forms without departing from the spirit of the invention. For example, the collapsible membrane may be embodied in forms and configurations other than those illustrated or described herein. Accordingly, all changes which come within the scope of the claims are intended to be embraced therein.

What is claimed is:

1. An insert for a vacuum device which applies suction to a body part, the vacuum device including a shell having an interior adapted to be applied over the body part, comprising:

a liner insert portion generally conforming to the interior of the shell and forming a liner between the shell and the body part;

a collapsible insert portion forming an enclosure, with an opening defined in the enclosure which communicates with a source of vacuum;

a passageway defined within the insert which communicates with the body part;

the collapsible insert portion isolating the passageway and the body part from the source of vacuum, with vacuum from the source of vacuum causing the collapsible portion to collapse and thereby transmit the vacuum as a suction force within the shell to pull on the body part.

2. The insert of claim 1 wherein the liner insert portion further includes an extension portion, the liner insert portion including the extension portion and the collapsible insert portion being formed integral, and the passageway is defined between the collapsible insert portion and the extension portion.

3. The insert of claim 1 wherein the liner insert portion has a funnel shape which generally conforms to the interior shape of the shell and further includes an extension portion forming the tubular part of the funnel shape, with the collapsible insert portion being formed within the extension portion, the liner insert portion including the extension portion and the collapsible insert portion being formed integral, and the passageway is defined between the collapsible insert portion and the extension portion.

4. The insert of claim 3 further including a valve formed integral with the extension portion, the valve closing under the influence of vacuum within the shell.

5. A breast shield assembly for use in expressing breastmilk using a vacuum source, comprising:

a shell having an interior adapted to be applied over the breast;

a liner portion generally conforming to the interior of the shell and forming a liner between the shell and the breast;

a collapsible portion forming an enclosure, with an opening defined in the enclosure which communicates with the vacuum source;

a passageway defined within the liner portion which communicates with the breast for milk flow through the passageway;

the collapsible portion isolating the passageway and the breast from the vacuum source, with vacuum from the vacuum source causing the collapsible portion to collapse and thereby transmit the vacuum as a suction force within the shell to pull on the body part.

6. The breast shield assembly of claim 5 wherein the liner portion has a funnel shape with a hemispherical part which generally conforms to the interior shape of the shell and further includes an extension portion extending from the hemispherical part, with the collapsible portion being formed within the extension portion, the liner portion including the extension portion and the collapsible portion being formed integral as an insert which is removably attachable to the shell, with the passageway defined between the collapsible insert portion and the extension portion.

7. The breast shield assembly of claim 6 further including a valve formed integral with the extension portion and communicating with the passageway, the valve closing under the influence of vacuum within the shell.

8. A breast shield assembly for use with a vacuum source comprising:
   a hood body having an outer rim within which a breast is received, and
      a hood extension portion extending downstream from the outer rim; and
   a vacuum isolation element including a collapsible membrane portion, a liner portion which attaches to the outer rim, and a portion defining a passageway to the breast located within the hood extension portion of the hood body, the collapsible membrane portion having an interior cavity adapted to be connected to the vacuum source and being effective to communicate a negative pressure from the vacuum source to within the shield extension portion when in a collapsed state and to isolate the vacuum source from the breast.

9. The breast shield of claim 8 wherein the vacuum isolation element is a one-piece removable insert.

10. A breast shield assembly for use with a vacuum source comprising:
   a hood body having an outer rim within which a breast is received, and
      a hood extension portion extending downstream from the outer rim;
   a milk drain connected to the hood extension portion;
   a collector for expressed milk connected to the milk drain; and
   an insert attached to the outer rim and the shield extension portion of the hood body, the insert having a funnel shaped portion including an insert extension portion, a collapsible membrane portion and a valve which opens and closes, the insert extension portion further defining a milk passageway to the valve, the funnel shaped portion generally conforming in shape to the outer rim of the hood body, the insert extension portion including the collapsible membrane portion being located within the hood extension portion and forming an enclosure within the hood body isolating the vacuum source from expressed milk, the collapsible membrane portion communicating with and transmitting air pressure changes from the vacuum source to the breast within the funnel shaped portion, and milk being directed through the milk passageway through the valve and to the collector.

11. The breast shield of claim 10 wherein the insert is removably attached to the outer rim.

12. The breast shield of claim 11 wherein the collapsible membrane portion has a substantially cylindrical shape and is located in an upper part of the insert extension portion, and the milk passageway is located in a lower part of the insert extension portion.

13. The breast shield of claim 12 wherein the valve comprises a duck-bill type valve.

14. The breast shield of claim 12 wherein the milk drain is formed in a rear portion of the insert extension portion.

15. The breast pump of claim 14 wherein the insert extension portion defines a volume and the collapsible membrane portion occupies greater than 50% of the volume when not in a collapsed state.

16. A breast shield assembly for use in expressing breastmilk using a vacuum source, comprising:
   a shell having an interior adapted to be applied over the breast;
   a funnel shaped portion having a hemispherical part generally conforming to the interior of the shell and forming a liner between the shell and the breast, and a tubular extension portion extending from the hemispherical part;
   a collapsible portion forming an enclosure, with an opening defined in the enclosure which communicates with the vacuum source, with the collapsible portion being formed within the extension portion;
   a passageway defined between the collapsible portion and the extension portion which communicates with the breast for milk flow through the passageway, the insert portion isolating the passageway and the breast from the vacuum source, with vacuum from the vacuum source causing the collapsible portion to collapse and thereby transmit the vacuum as a suction force within the shell to pull on the breast;
   the funnel shaped portion including the extension portion, and the collapsible portion being formed integral and adapted as an insert which is removably attached to the shell.

17. The breast shield assembly of claim 16 further including a valve formed integral with the extension portion and communicating with the passageway, the valve closing under the influence of vacuum within the shell.

18. A breast pump comprising:
   a shield having an outer rim within which a breast is received, and a
      shield extension portion extending downstream from the outer rim;
   a milk drain connected to the shield extension portion;
   a collector for expressed milk connected to the milk drain; and
   a monolithic insert attached to the outer rim and located within the shield extension portion of the hood body, the insert having a funnel shaped portion including an insert extension portion, a collapsible portion, a passageway defined by the insert extending from the funnel shaped portion, and a valve which opens and closes the passageway, the funnel shaped portion generally conforming in shape to the outer rim of the hood body, the insert extension portion including the collapsible portion being located within the shield extension portion and forming an enclosure within the insert adapted to isolate a vacuum source communicating with the shield from expressed milk, with the collapsible portion communicating with and transmitting air pressure changes from a vacuum source to the shield, and milk being directed through the passageway to the milk drain and the collector.

19. The breast pump of claim 18 wherein the collapsible portion has a substantially cylindrical shape.

20. The breast pump of claim 18 wherein the insert is disposable and formed from a substantially resilient material.

* * * * *